US00PP23696P3

(12) United States Plant Patent
Antcliff et al.

(10) Patent No.: US PP23,696 P3
(45) Date of Patent: Jul. 2, 2013

(54) GRAPEVINE PLANT NAMED 'M 48-42'

(50) Latin Name: *Vitis hybrida*
Varietal Denomination: M 48-42

(75) Inventors: Allan J. Antcliff, Mildura (AU); Veronica R. Antcliff, legal representative, Scone (AU); Gillian M. Williams, legal representative, Swan Hill (AU); Susan R. Antcliff, legal representative, Ainslie (AU); Judith R. Antcliff, legal representative, Mildura (AU); Peter J. Antcliff, legal representative, Canberra (AU); Peter R. Clingeleffer, Glen Osmond (AU)

(73) Assignee: Commonwealth Scientific and Industrial Research Organisation, Australian Capital Territory (AU)

( * ) Notice: Subject to any disclaimer, the term of this patent is extended or adjusted under 35 U.S.C. 154(b) by 0 days.

(21) Appl. No.: 13/137,136

(22) Filed: Jul. 22, 2011

(65) Prior Publication Data

US 2012/0192322 P1 Jul. 26, 2012

(30) Foreign Application Priority Data

Jan. 25, 2011 (AU) ..... PBR 2011018

(51) Int. Cl.
*A01H 5/00* (2006.01)

(52) U.S. Cl.
USPC ..... Plt./205

(58) Field of Classification Search
USPC ..... Plt./205, 206
See application file for complete search history.

*Primary Examiner* — Howard Locker
(74) *Attorney, Agent, or Firm* — Buchanan Ingersoll & Rooney PC

(57) ABSTRACT

A new and distinct variety of diploid grapevine is provided which abundantly forms early-ripening juicy relatively large bunches of small substantially spherical berries that develop an intense black-purple coloration upon maturity. A propensity for high stenospermocarpic fruit production is displayed. Superior resistance to downy mildew and powdery mildew has been observed during evaluations to date. The plant is particularly well suited for the production of dried currants. The fruit also can be used in the table grape market or be used to make wine or grape juice.

5 Drawing Sheets

Figure 1:
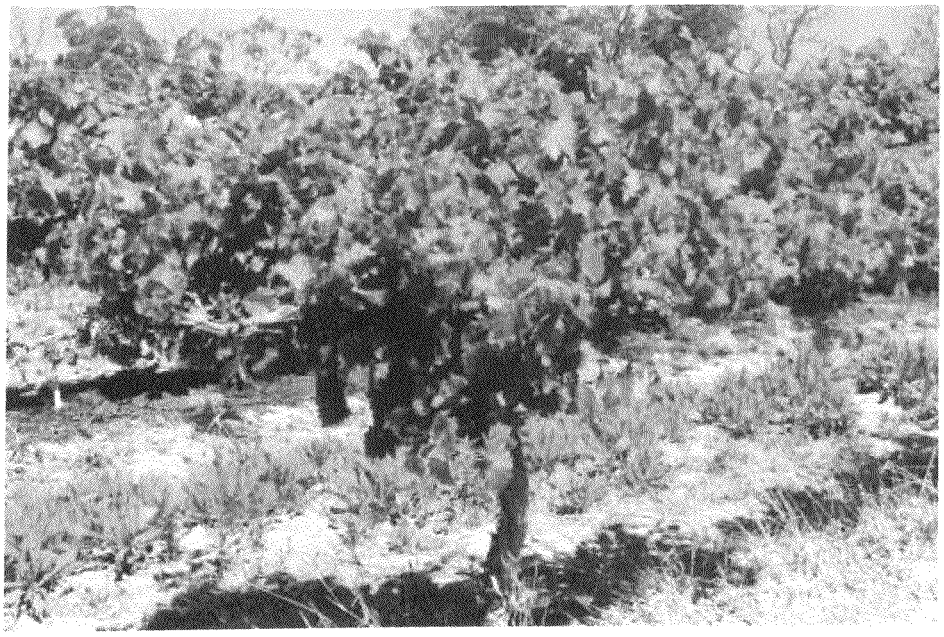

Botanical/commercial classification: *Vitis hybrida*/Grapevine.

Varietal denomination: cv. M 48-42.

BACKGROUND OF THE VARIETY

The new diploid grapevine variety of the present invention was created during the course of a grapevine breeding program that was carried out in Australia wherein two parents were crossed which previously had been studied in the hope that they would contribute the desired characteristics. The female parent (i.e., seed parent) was the complex hybrid *Vitis* spp. '39-639 Seyve-Villard' variety (non-patented in the United States). Such female parent is listed in Galet, P., "Cépages et vignobles de France, Tome I Les Vignes Américaines" (1988) as being an early-maturing, disease resistant white-berried interspecific hybrid of unknown origin. The female parent was chosen as a seed parent primarily in view of its resistance to mildew diseases, such as downy mildew and powdery mildew. The male parent (i.e., pollen parent) was the 'Beauty Seedless' variety (non-patented in the United States). The 'Beauty Seedless' variety is recognized for its ability to produce with high productivity bunches of early-ripening stenospermocarpic egg-shaped berries having a distinctive light spicy flavor. The parentage of the new variety of the present invention can be summarized as follows:

'39-639 Seyve-Villard' *Vitis* spp. Complex Hybrid×
'Beauty Seedless' *Vitis vinifera*.

The controlled cross that resulted in the production of the new variety of the present invention was carried out during Spring 1980 (Southern Hemisphere). Flowers of the female parent were emasculated and were thereafter protected from unintended cross-pollination by enclosure in pollen-proof bags. Approximately twenty-four hours following emasculation, pollen from the male parent was applied to the receptive stigma of the female parent. Such pollen had been collected from unopened flowers of male parent, and thereafter was dried in Petri dishes at 40° C. under conditions where contamination by other *Vitis* pollen was precluded. The resulting seeds from the cross were extracted from the fruits in Autumn 1981 (Southern Hemisphere) and were sown in a greenhouse while employing standard seed bed conditions. Emergent seedlings were transferred to standard potting mix and were maintained in pots under greenhouse conditions until they were planted in a vineyard during Spring 1981 (Southern Hemisphere). Thereafter, the plants were grown and evaluated while using standard grapevine cultivation conditions.

A single plant of the new variety was selected during 1988 from among the resulting siblings. The new variety was found to possess a combination of characteristics unlike that of its siblings and unlike that of either of the respective parent plants. The resulting plant has been carefully observed, tested and evaluated in replicated plantings and trials while growing on its own roots or when top-worked onto a range of grape rootstocks including *Vitis champinii* 'Ramsey' (non-patented in the United States).

It was found that the new grapevine of the present invention displays the following combination of characteristics:

(a) displays high stenospermocarpic fruit production,
(b) forms early-ripening juicy relatively large bunches of small substantially spherical berries that develop an intense black-purple coloration upon maturity,
(c) displays superior resistance to downy mildew and powdery mildew, and
(d) is particularly well suited for the production of dried currants.

Vines of the new variety have been found to be very fruitful with cane pruning systems being recommended for trellis drying.

The new variety well meets the needs of the horticultural industry. It can be grown to advantage for the production of dried vine fruit. It also may be used for the production of table grapes or used for making wine or grape juice.

The dried berries of the new variety have been shown to advantageously possess high levels of antioxidants. The 'Zante' and 'Carina' varieties (both non-patented in the United States) have previously commonly been used for the production of dried currants in Australia. When the hydrophilic oxyradical scavenging capacity of the fruit of these varieties was compared with that of the new variety, this capacity for the new variety was found to be approximately three times that of the 'Zante' variety and approximately 30 percent higher than that of the 'Carina' variety.

Vines of the new variety have displayed superior resistance to downy mildew (*Plasmopara vitriola*) and powdery mildew (*Uncinula necator*) when compared to other commonly grown grape varieties. For instance, when the new variety was compared at Merbin, NW Victoria, Australia, to the 'Sultana' variety (non-patented in the United States) under conditions conducive to disease infestations while using IPGRI Descriptors for Grapevine (1997), the comparative field ratings were obtained as follows:

| | 'Sultana' | Present Variety |
|---|---|---|
| Downy Mildew | 4.6 to 5.8 | 1.8 to 2.2 |
| Powdery Mildew | 6.6 to 7.0 | 3.8 to 4.2 |

The reported values are without units and are in accordance with the standard IPGRI Disease Rating Scale. Lower ratings are recognized to be indicative of increased resistance of the vine to disease infection and are not a percentage of infected plants. Field ratings similar to those of 'Sultana' have been observed for the 'Beauty Seedless' variety.

The new variety of the present invention does not require the use of a setting spray as other grape varieties commonly used to produce dried currants, such as the 'Zante' variety. Also, the new variety can be grown with reduced agrichemical usage making it well suited for organic grape production.

The new variety can be grown on its own roots or when grafted on standard rootstocks, such as 'Ramsey', 'Paulsen', 'Schwarzmann', and '140R' (each non-patented in the United States). When grown in northwest Victoria, Australia on 'Ramsey' rootstock, it is estimated that the vigor is increased by approximately 50 percent with a commensurate increase in yield.

The new variety of the present invention can be readily distinguished from its parental varieties upon an inspection of the fruit. More specifically, the grapes of the '39-639 Sayve-Villard' variety are larger, possess seeds, are unsuitable for drying to produce currants, and are borne in smaller bunches. The 'Beauty Seedless' variety forms larger black berries that are unsuitable for drying to produce currants, and is considerably more susceptible to downy mildew and powdery mildew.

The new variety of the present invention has been found to undergo asexual propagation at Irymple and Cardross, NW Victoria, Australia, by a number of routes including budding, top-working, and the rooting of cuttings. Accordingly, the new variety has been found to undergo asexual propagation in a true-to-type manner. During such propagation, the new variety has been found to be compatible with a wide range of rootstocks. Grafting has been found to make possible optimum vigor and canopy cover.

The new variety initially was named 'M 48-42', and sometimes has been identified as 'Black Gem'.

DETAILED DESCRIPTION OF PHOTOGRAPHS

The accompanying photographs show, as nearly true as it is reasonably possible to make the same in color illustrations of this character, typical specimens of the new variety.

Figure 2:
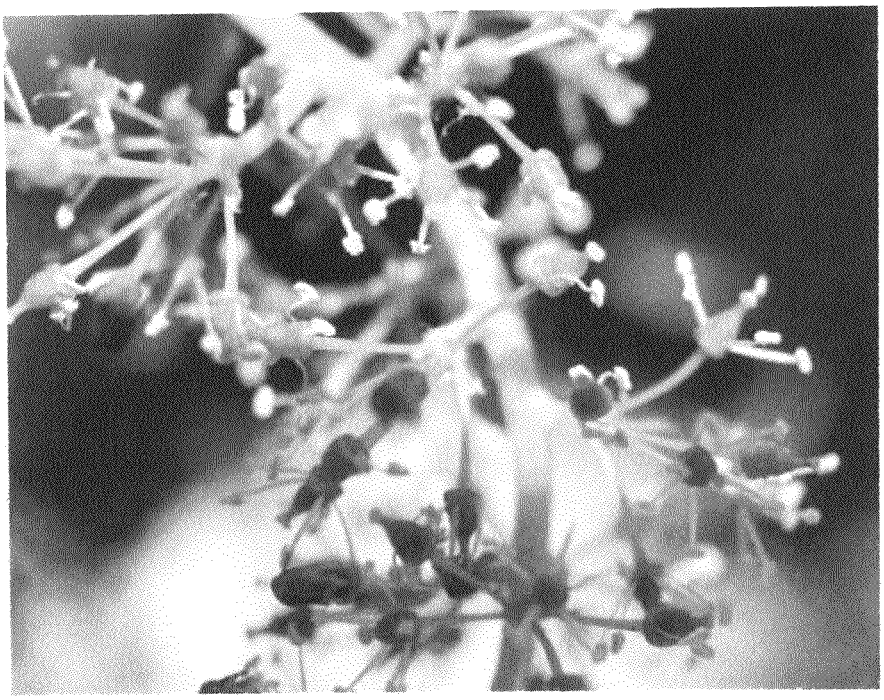
Figure 3:
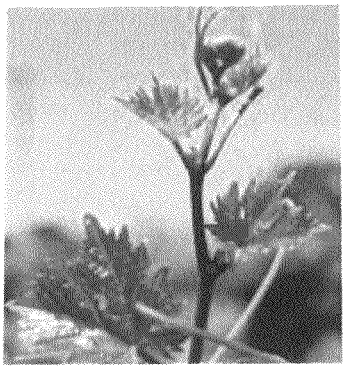
Figure 4:
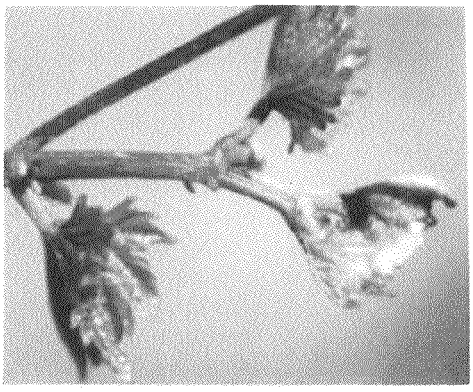
Figure 5:
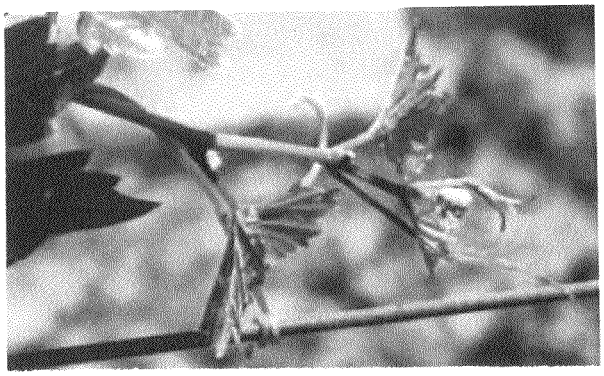
Figure 6:
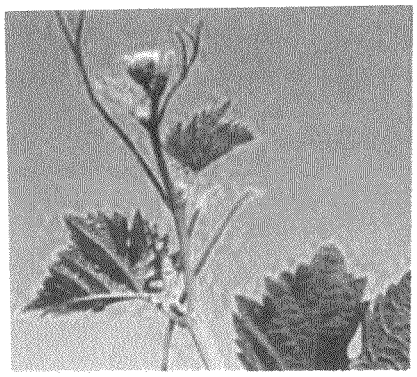
Figure 7:
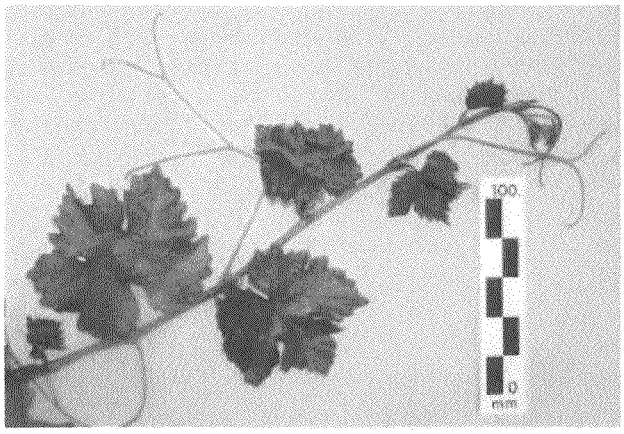
Figure 8:
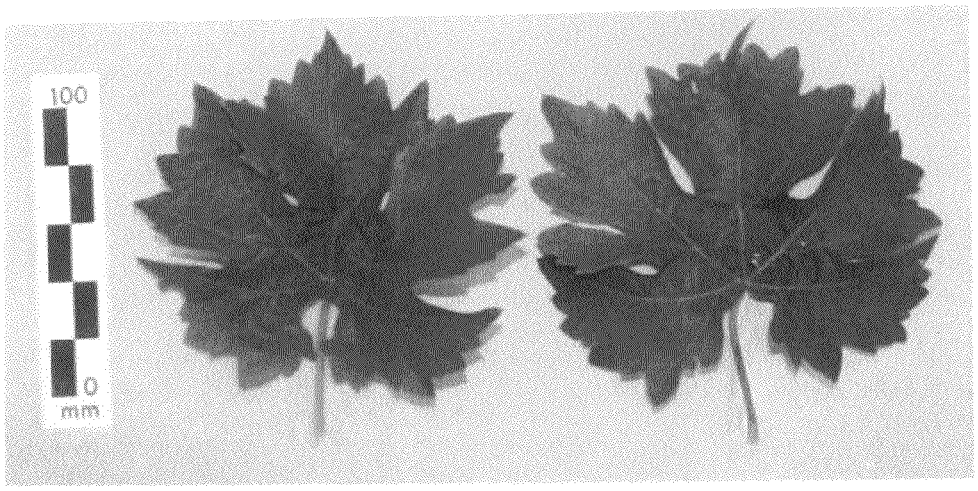
Figure 9:
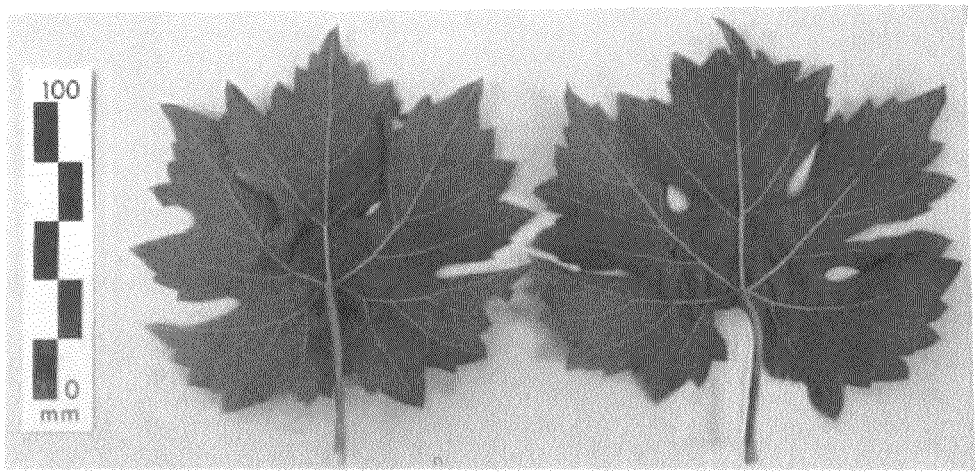

FIG. 1—illustrates the typical vine growth habit at the time of flowering wherein the formation of a dense canopy is illustrated;

FIG. 2—illustrates a close view of typical inflorescence wherein individual flowers are shown;

FIG. 3—illustrates a typical shoot tip wherein some anthocyanin coloration is apparent;

FIG. 4—illustrates another view of a typical shoot tip;

FIG. 5—illustrates a shoot tip wherein typical tendril attachment is included;

FIG. 6—illustrates another view of a shoot tip with upright extending tendrils;

FIG. 7—illustrates a typical young shoot with young foliage and tendrils together with the inclusion of dimensions in millimeters for comparative purposes;

FIG. 8—illustrates a pair of typical mature leaves (adaxial surfaces) wherein dimensions in millimeters are included for comparative purposes;

FIG. 9—illustrates a pair of typical mature leaves (abaxial surfaces) wherein dimensions in millimeters are included for comparative purposes.

Figure 10:
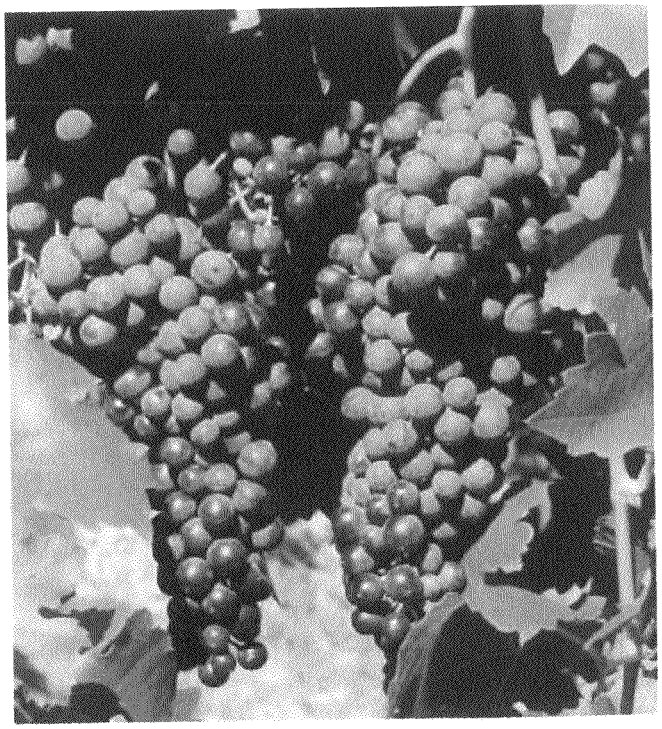
Figure 11:
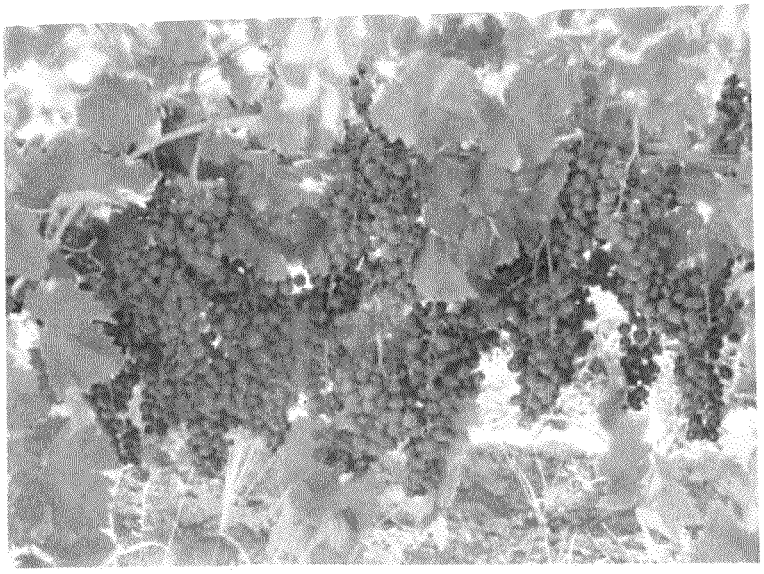
Figure 12:
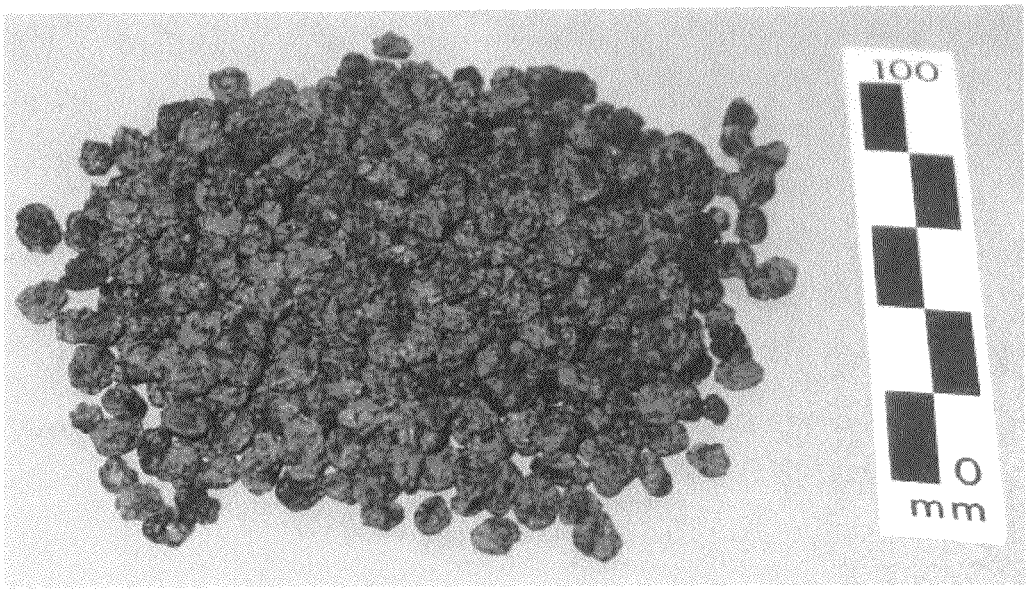

FIG. 10—illustrates a close view of typical mature berry clusters showing the natural berry characteristics;

FIG. 11—illustrates a number of typical hanging clusters of berries together with foliage; and FIG. 12—illustrates a mound of typical dried berries wherein dimensions in millimeters are included for comparative purposes.

DETAILED DESCRIPTION

The following description is based upon the observation of representative year-old plants of the new variety while growing on their own roots in Australia. Color terminology is in accordance with The R.H.S. Colour Chart (1966 Edition or equivalent) of The Royal Horticultural Society (London) in association with the Flower Council of Holland (Leiden). Common color terms are to be accorded their customary dictionary significance.

Vine:

*Foliage buds.*—Color: Yellow-Green Group 148B.

*Young shoots.*—Time of bud burst: early. Form of tip: half-open to wide-open. Color: Greyed-Orange Group 166A. Density of prostrate hairs on tip: medium to dense. Erect hairs on tip: absent or very sparse.

*Mature shoots.*—Attitude: substantially erect. Color before delignification: Yellow-Green Group 150C. Color of dorsal side of internode: Yellow-Green Group 148B with red stripes of Greyed-Red Group 178A. Color of ventral side of internode: completely green. Color of dorsal side of node: green with red stripes. Color of ventral side of node: commonly completely green, and sometimes green with red stripes. Erect hairs on node: absent to very sparse. Erect hairs on internode: absent. Density of prostrate hairs on node: very sparse. Density of prostrate hairs on internode: very sparse to medium. Number of consecutive tendrils: commonly up to two per standard UPOV descriptor. Length of tendril: short, with lengths of 14 to 16 cm on average commonly being observed. Length of internodes: medium, commonly approximately 1.2 cm. Growth of axillary shoots: weak.

*Young leaves.*—Color of upper surface: Greyed-Orange Group 165A with bronze anthocyanin. Color of under surface: Greyed-Orange Group 166A with bronze anthocyanin. Prostrate hairs between veins: absent. Erect hairs between veins: absent. Density of prostrate hairs on main veins: very sparse to sparse. Erect hairs on main veins: absent.

*Mature leaves.*—Length: approximately 8.3 cm on average. Width (top): approximately 10.2 cm on average. Width (bottom): approximately 11.5 cm on average. Blade shape: orbicular, or alternatively termed pentagonal. Lobe number: five. Color of upper surface: Green Group 137A. Color of under surface: Green Group 137C. Veins on upper surface: Yellow-Green Group 144A. Veins on under surface: Yellow-Green Group 144A. Anthocyanin coloration of main veins on upper surface: not present. Blistering of blade upper surface: absent or weak when present. Shape of teeth: both sides convex. Length of teeth: long. Ratio length/width of teeth: medium. General shape of petiole sinus: half to strongly overlapping. Tooth at petiole sinus: present. Petiole length: commonly approximately 5.6 cm on average. Petiole sinus: mainly open and V-shaped at base; however, closed on some leaves. Petiole sinus limited by veins: not present. Shape of upper lateral sinus lobes: mainly open and V-shaped at base with some closed. Depth of upper lateral sinus: medium. Density of prostrate hairs between veins: very sparse. Erect hairs between veins: absent. Density of prostrate hairs on main veins: sparse. Erect hairs on main veins: absent. Length of petiole compared to middle vein: shorter to equal.

*Young shoots.*—Surface: striate. Primary color: Greyed-Orange Group 166A.

*Mature canes.*—Primary color: Greyed-Orange Group 166B.

Inflorescence:

*Time.*—At South Merbein, Victoria, Australia, first bloom occurs during the last week of October in an average season and full bloom commonly occurs during the first week of November in an average season. Gynoecium: color of Green Group 143B when unset.

*Buds.*—Green Group 141C in coloration.

*Flowers.*—Number per shoot: commonly approximately 1.1 to 2 on average. Sex: male and female parts fully developed.

*Peduncle.*—Length: short, commonly approximately 40 to 60 mm measuring the shoulder branch.

*Pedicel.*—Length: commonly approximately 4.8 mm on average.

*Bunches.*—Shape: somewhat conical with a dominant shoulder, sometimes termed a winged cluster. Productivity: yields of approximately 15 tonnes/ha have been observed for own-rooted vines, and approximately 30 tonnes/ha on vines grafted to *Vitis champinii* 'Ramsey' rootstock. Percentage of berry set: low, and commonly 20 to 30 percent. Single cluster/bunch weight: medium to high, and commonly 40 to 70 g on average. Cluster/bunch length: medium, a cluster commonly is approximately 100 to 175 mm in length on average without peduncle. Width: a cluster commonly is approximately 100 mm in width on average including the wing. Density: relatively loose.

*Berries.*—Ripening season: early. In an average season, typically during the last week of January at South Merbein, Victoria, Australia. Size: small. Length: typically approximately 11.5 mm on average. Width: typically approximately 10.8 mm on average. Number: commonly approximately 135 berries per cluster. Weight: commonly 0.6 to 0.9 g per single berry on average. Shape: substantially circular. Skin thickness: relatively thick. Presence of seeds: seedless to rudimentary formation. Skin color (with bloom): Black Group 202B. Skin color (without bloom): Black Group 202A. Mature flesh color: White Group 155D. Anthocyanin coloration of flesh: weak. Juiciness of flesh: very juicy. Firmness of flesh: soft. Particular flavor: sweet with peppery spice. Pedicel length: intermediate. Ease of detachment from pedicel: somewhat difficult. Sugar content of must: high, commonly near 21 percent. Acid content of must: low (0.5 percent tartrate). Flavor: non-distinctive.

*Seeds.*—Commonly absent, or soft/rudimentary when rarely present.

Biotic stress susceptibility: During evaluation to date the following has been observed.

*Botrytis cinerea—Noble Rot.*—Low on leaves and low on fruit.

*Plasmopara viticola—downy mildew.*—Few if any symptoms on leaves and fruit.

*Uncinula necator—powdery mildew.*—Few if any symptoms on leaves and fruit.

*Elsinoe ampelina—anthracnose.*—Never observed.

*Entypa lata—dieback.*—Never observed.

*Phormopsis viticola—cane and leaf spot.*—Never observed.

Plants of the new 'M 48-42' variety have not been observed under all possible environmental conditions to date. Accordingly, it is possible that the phenotypic expression may vary somewhat with changes in light intensity and duration, cultural practices, and other environmental conditions.

We claim:

1. A new and distinct grape plant characterized by the following combination of characteristics:

(a) displays high stenospermocarpic fruit production, (b) forms early-ripening juicy relatively large bunches of small substantially spherical berries that develop an intense black-purple coloration upon maturity, (c) displays superior resistance to downy mildew and powdery mildew, and (d) is particularly well suited for the production of dried currants;

substantially as shown and described.

* * * * *